(12) United States Patent
Jones

(10) Patent No.: US 6,248,928 B1
(45) Date of Patent: Jun. 19, 2001

(54) METALORGANIC CHEMICAL VAPOR DEPOSITION PRECURSORS

(75) Inventor: Anthony Copeland Jones, Merseyside (GB)

(73) Assignee: Inorgtech Limited, Mildenhall (GB)

( * ) Notice: Subject to any disclaimer, the term of this patent is extended or adjusted under 35 U.S.C. 154(b) by 0 days.

(21) Appl. No.: 09/620,855

(22) Filed: Jul. 21, 2000

(30) Foreign Application Priority Data

Jul. 23, 1999 (GB) ................................................ 9917189

(51) Int. Cl.⁷ ..................................................... C07C 45/61
(52) U.S. Cl. ........................................... 568/318; 568/396
(58) Field of Search ..................................... 568/318, 396

(56) References Cited

U.S. PATENT DOCUMENTS 5,453,494 * 9/1995 Kirlin et al. .
5,518,536 * 5/1996 Doellein .

* cited by examiner

*Primary Examiner*—Johann Richter
*Assistant Examiner*—Sikarl A. Witherspoon
(74) *Attorney, Agent, or Firm*—Drinker Biddle & Reath LLP

(57) ABSTRACT

A method of manufacturing a strontium β-diketonate precursor suitable for MOCVD techniques comprises the step of reacting strontium with a sterically hindered alcohol to produce strontium alkoxide, subsequently reacting the strontium alkoxide with a β-diketone to form a strontium β-diketonate alcohol adduct and removing the alcohol from the adduct.

8 Claims, 3 Drawing Sheets

METALORGANIC CHEMICAL VAPOR DEPOSITION PRECURSORS

DESCRIPTION

This invention concerns a method for manufacturing precursors for use in metalorganic chemical vapour deposition (MOCVD) techniques.

Strontium bis-tetramethylheptanedionate, Sr(thd)$_2$, has important applications as a precursor for growth of ferroelectric, dielectric and superconducting oxide films by MOCVD. Examples of these oxides are barium strontium titanate, (Ba,Sr) TiO$_3$, and strontium bismuth tantalate, SrBi$_2$Ta$_2$O$_9$.

MOCVD precursors should be volatile and evaporate cleanly without leaving any significant involatile residues. The precursors should also be pure i.e. free from extraneous organic impurities, which might interfere with the MOCVD process.

In the case of Group IIA β-diketonate precursors, such as Sr(thd)$_2$, the purity of the compound and evaporation characteristics are critically dependent on the method of manufacture of the precursor.

Group IIA β-diketonates may be prepared by an aqueous route, such as by addition of β-diketone to an aqueous solution of metal chloride or metal hydroxide or by addition of Na(thd) to hydrated metal chloride.

However, these routes are unsuitable for producing precursors for MOCVD as they lead to hydrated species, which form involatile residues on evaporation during MOCVD. This is a serious problem as it leads to changes in the precursor gas-phase concentration over time and having poor uniformity oxide layers.

Preferred routes to producing high purity Group IIA β-diketonates are, therefore, non-aqueous and are carried out in hydrocarbon or alcohol solvents with rigorous exclusion of air and moisture during synthesis.

An alternative non-aqueous route called 'labile ligand displacement' has been proposed for producing Sr(thd)$_2$.

The theoretical process is as follows:

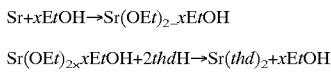

Sr(OEt)$_2$·xEtOH+2thdH→Sr(thd)$_2$+xEtOH

However, the resultant precursor is not Sr(thd)$_2$ but a trimeric species {Sr(thd)$_2$}$_3$ (thdH), which contains adducted neutral thdH ligand. This ligand is lost during evaporation of the precursor during MOCVD, which is an undesirable complication in the process. FIG. 1 of the accompanying drawings illustrates the effect.

An object of this invention is to provide a method of manufacturing a strontium β-diketonate precursor suitable for use in MOCVD techniques.

According to this invention there is provided a method of manufacturing a strontium β-diketonate precursor suitable for use in MOCVD techniques comprising the steps of reacting strontium with a sterically hindered alcohol to produce strontium alkoxide, subsequently reacting the strontium alkoxide with a β-diketone to form a strontium β-diketonate alcohol adduct and removing the alcohol from the adduct.

The alcohol used in the reaction may also serve as solvent for the reaction.

The alcohol chosen for use in the method of the invention is preferably a secondary or tertiary alcohol in order to provide the desired steric hindrance. Iso-propanol is a preferred alcohol for use in the invention, although other bulky alcohols such as iso-butanol or tertiary butanol may also be suitable. Indeed any alcohol more sterically hindered than methanol or ethanol could be suitable for use in the method of the invention.

The β-diketone used in the method of the invention preferably has the formula

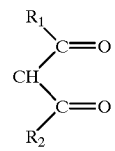

wherein R$_1$ and R$_2$ are the same or different and are straight or branched, optionally substituted, alkyl groups or, optionally substituted, phenyl groups. Example of suitable substituents include chlorine, fluorine and methoxy.

Examples of suitable β-diketones for use in the method of the invention include the following:

| R$_1$ | R$_2$ | |
|---|---|---|
| CH$_3$ | CH$_3$ | acetylacetone (acacH) |
| CF$_3$ | CH$_3$ | trifluoroacetylacetone (tfacH) |
| CF$_3$ | CF$_3$ | hexafluoroacetylacetone (hfacH) |
| CH$_3$ | C(CH$_3$)$_3$ | dimethylheptanedione (dhdH) |
| C(CH$_3$)$_3$ | C(CH$_3$)$_3$ | tetramethylheptanedione (thdH) |
| CH$_3$ | CF$_2$CF$_2$CF$_3$ | heptafluoroheptanedione (fhdH) |
| CF$_2$CF$_2$CF$_3$ | CF$_2$CF$_2$CF$_3$ | tetradecafluorononanedione (tdfndH) |
| C(CH$_3$)$_3$ | CF$_3$ | trifluorodimethylhexanedione (tpmH) |
| CF$_3$ | CF$_2$CF$_3$ | octafluorohexanedione (ofhdH) |
| C(CH$_3$)$_3$ | CF$_2$CF$_3$ | pentafluorodimethylheptanedione (ppm) |
| CF$_3$ | CF$_2$CF$_2$CF$_3$ | decafluoroheptanedione (dfhd) |
| C(CH$_3$)$_3$ | CH$_2$CH$_2$CH$_2$OCH$_3$ | dimethylmethoxyoctanedione (dmmodH) |
| CCl$_3$ | CH$_3$ | trichloropentanedione (tclacH) |
| Ph | Ph | diphenylpropanedione (dppH) |

The preferred β-diketone for use in produding a strontium precursor for MOCVD according to the invention is tetramethylheptanedione (thdH).

It is believed that the use of a sterically hindered alcohol as reactant and solvent leads to the formation initially of Sr(thd)$_2$—alcohol adduct as an intermediate, which prevents formation of unwanted [Sr(thd)$_2$] thdH adduct as a product.

BRIEF DESCRIPTION OF THE DRAWINGS

This invention will now be further described, by way of example only, with reference to the accompanying drawings. in which.

The invention will be yet further described by means of the following Example.

EXAMPLE 87.6 (1 mole) of strontium metal was dissolved in 3 liters of dry iso-propanol. The mixture was brought to the boil under reflux in order to dissolve all the strontium metal. 368 g (2 moles) of tetramethylheptanedione (thdH) was then added and the mixture stirred at room temperature for 1 hour.

The volume of the mixture was reduced to 800 cm$^3$ by vacuum distillation (50° C.) and the mixture set aside to crystallize.

Figure 3:
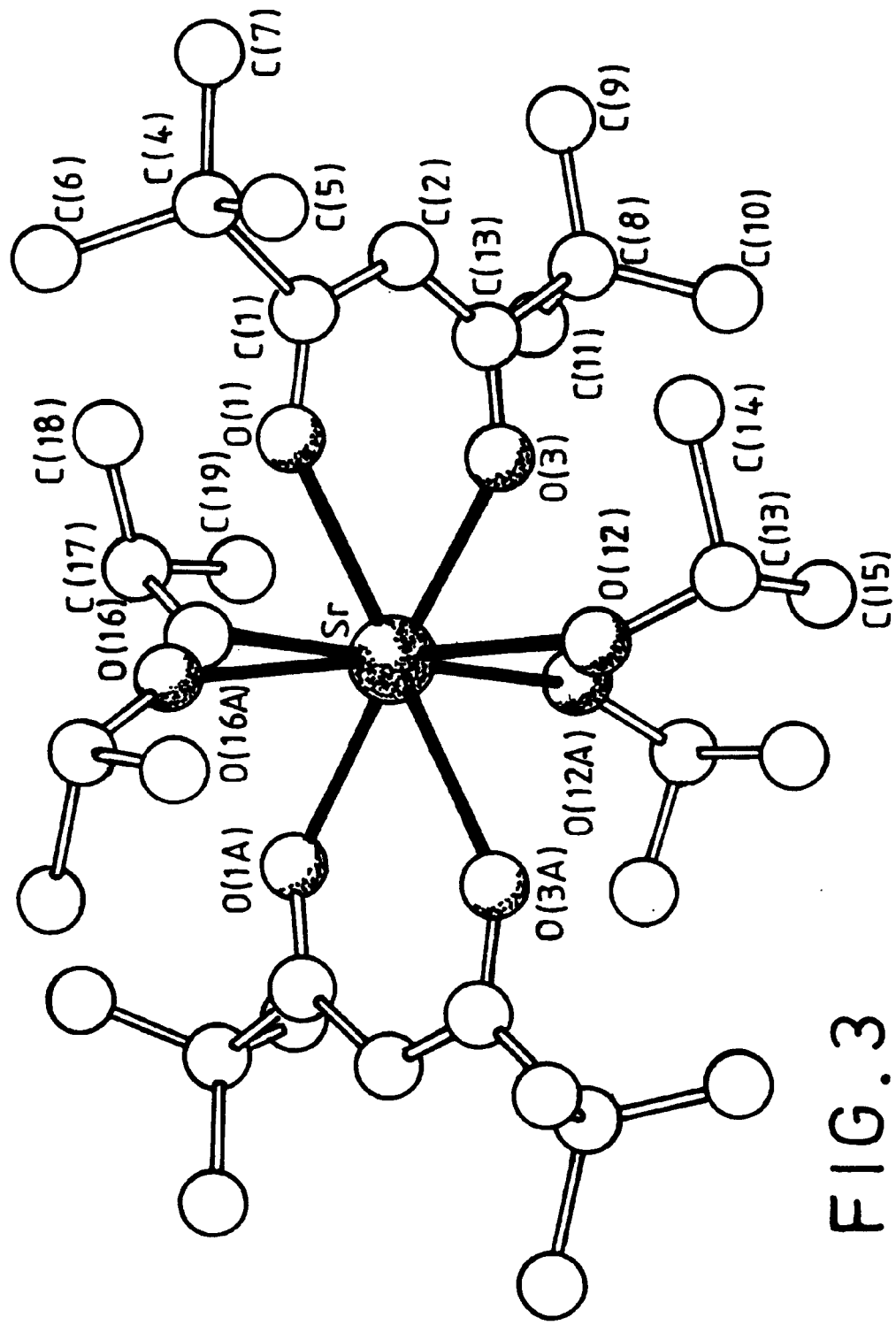
FIG. 3 shows the likely structure of the iso-propanol adduct of Sr(thd)2 formed as an intermediate in the method of the invention.

The resulting crystals were identified by x-ray diffraction as the monomeric iso-propanol adduct of Sr (thd)$_2$, [Sr(thd)$_2$] (i-PrOH). The structure for this adduct is shown in FIG. 3 of the drawings.

The yield was 295 g (65% based on Sr metal).

The crystals were then pumped under vacuum at between 30–80° C. to remove partially the adducted iso-propanol, resulting in a microcrystalline solid.

A 100 g portion of the monocrystalline solid was then dissolved in 1 liter of dry nonane. The solution was heated at 60° C. under reduced pressure (20 mm Hg) and the residual iso-propanol was removed by distillation at a head temperatue of approximately 23° C. The removal of iso-propanol was continued until the distillation lead temparature rose to approximately 54° C.

The volume of the nonane solution was reduced in vacuo (maximum temperature 65° C.) until crystals were seen to form in the reaction vessel. The mixture was then set aside to cool. The resulting crystals were filtered and dried in vacuo to give Sr(thd)2 as a white microcrystalline solid, which gave the following microanalysis results for four different samples:

| Predicted | Sample 1 | Sample 2 | Sample 3 | Sample 4 |
|---|---|---|---|---|
| % C 58.18 | 56.88 | 56.93 | 56.82 | 56.88 |
| % H  8.43 | 8.39 | 8.38 | 8.41 | 8.42 |

Figure 1:
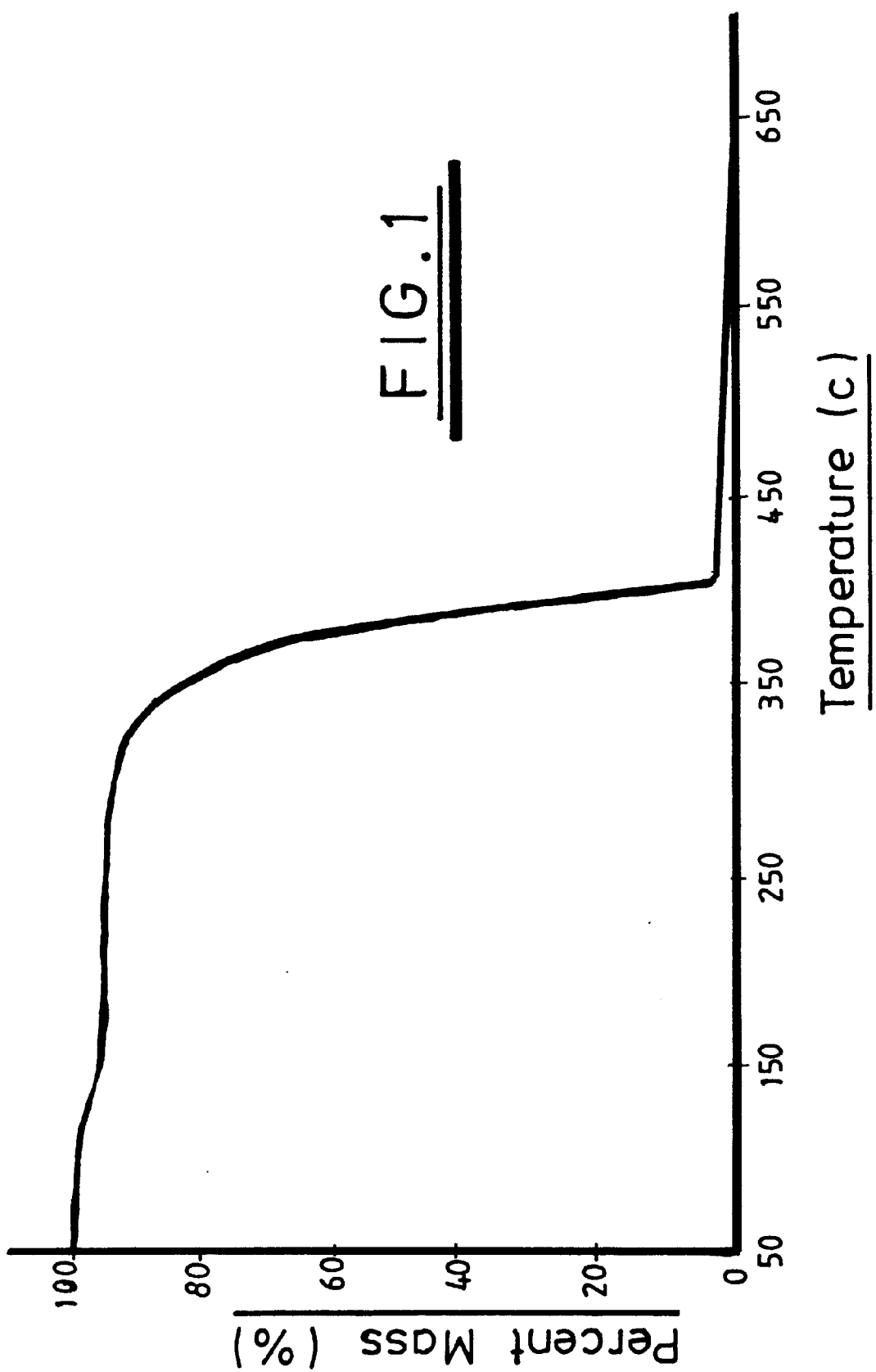
FIG. 1 is a graph showing evaporation characteristics of [Sr(thd)2]3 thdH made according to the prior art method.
Figure 2:
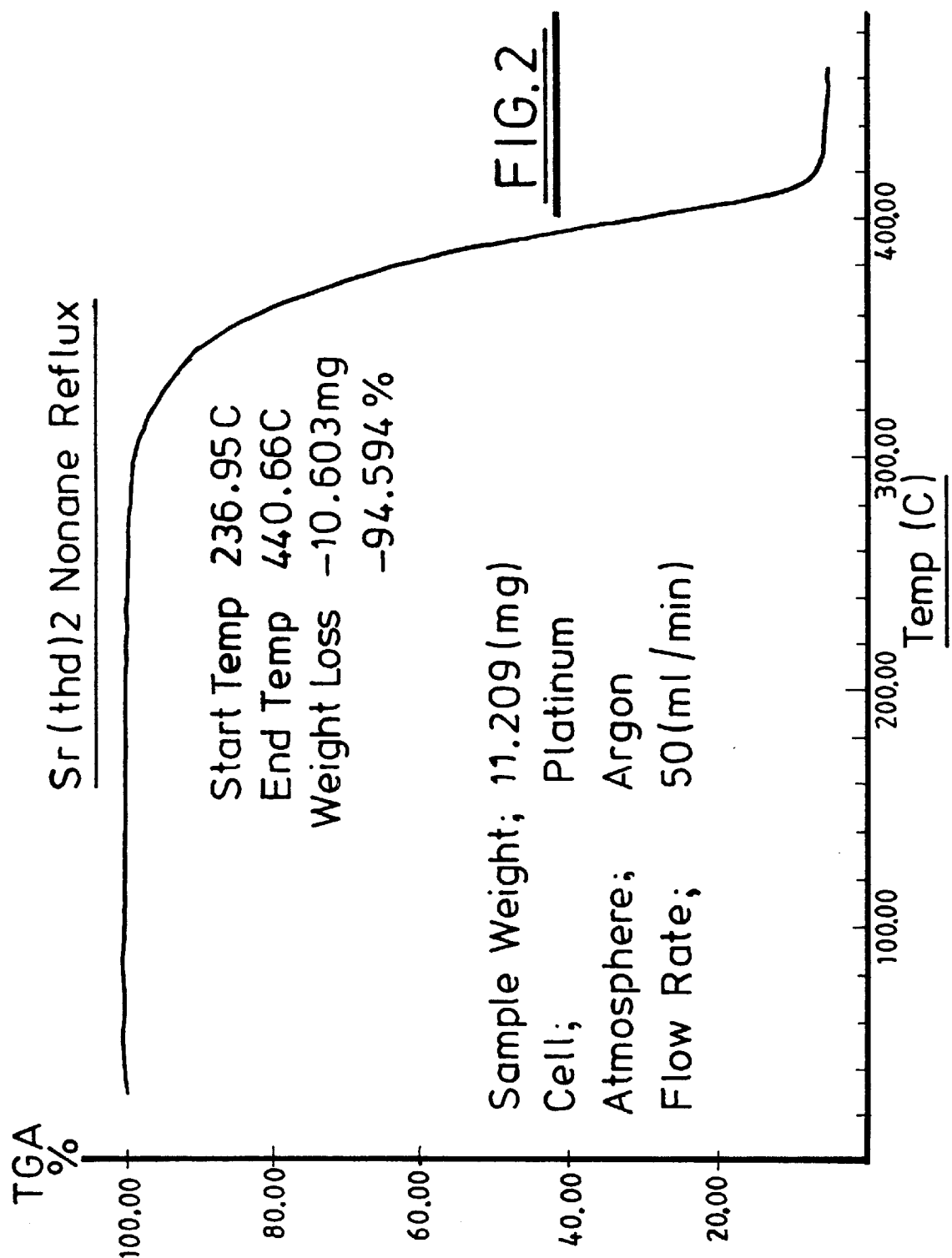
FIG. 2 is a graph showing evaporation characteristics of Sr(thd)2 made according to the invention.

The Sr(thd)$_2$ made in accordance with this Example evaporated cleanly as shown in FIG. 2 of the drawings. Evaporation of the prior art [Sr(thd)$_2$]$_3$ thdH as shown in FIG. 1 of the drawings shows loss of thd ligand at about 150° C. which is an unwanted complication in MOCVD techniques.

What is claimed is:

1. A method of manufacturing a strontium β-diketonate precursor suitable for use in MOCVD techniques comprising the steps of reacting strontium with a sterically hindered alcohol to produce strontium alkoxide, subsequently reacting the strontium alkoxide with a β-diketone to form a strontium β-diketonate alcohol adduct and removing the alcohol from the adduct.

2. A method as claimed in claim 1, wherein the alcohol used in the reaction serves as solvent for the reaction.

3. A method as claimed in claim 1 or 2, wherein the alcohol is selected from the group consisting of secondary and tertiary alcohol.

4. A method as claimed in claim 3, wherein the alcohol is selected from the group consisting of iso-propanol, iso-butanol and tertiary-butanol.

5. A method as claimed in claim 1, wherein the β-diketone has the following formula:

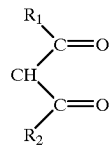

wherein R$_1$ and R$_2$ are the same or different and are selected from the group consisting of straight and branched, optionally substituted, alkyl groups and, optionally substituted, phenyl groups.

6. A method as claimed in claim 5, wherein the optional substituents are selected from the group consisting of chlorine, fluorine and methoxy.

7. A method as claimed in claim 5, wherein the β-diketone is selected from the group consisting of acetylacetone, trifluoroacetylacetone, hexafluoroacetylacetone, dimethylheptanedione, tetramethylheptanedione, heptafluoroheptanedione, tetradecafluorononanedione, trifluorodimethylehexanedione, octafluorohexanedione, pentafluorodimethylheptanedione, decafluoroheptanedione, dimethylmethoxyoctanedione, trichloropentanedione and diphenylpropanedione.

8. A method as claimed in claim 1, wherein the β-diketone is tetramethylheptanedione.

\* \* \* \* \*